US011298222B2

(12) United States Patent
Kaschke et al.

(10) Patent No.: US 11,298,222 B2
(45) Date of Patent: Apr. 12, 2022

(54) ARTIFICIAL EYE LENS WITH DIFFRACTIVE GRATING STRUCTURE AND METHOD FOR PRODUCING AN ARTIFICIAL EYE LENS

(71) Applicant: Carl Zeiss Meditec AG, Jena (DE)

(72) Inventors: Michael Kaschke, Oberkochen (DE); Manfred Dick, Gefell (DE); Mario Gerlach, Glienicke-Nordbahn (DE)

( * ) Notice: Subject to any disclaimer, the term of this patent is extended or adjusted under 35 U.S.C. 154(b) by 73 days.

(21) Appl. No.: 16/616,028

(22) PCT Filed: May 17, 2018

(86) PCT No.: PCT/EP2018/062920
§ 371 (c)(1),
(2) Date: Nov. 22, 2019

(87) PCT Pub. No.: WO2018/219669
PCT Pub. Date: Dec. 6, 2018

(65) Prior Publication Data
US 2020/0085569 A1    Mar. 19, 2020

(30) Foreign Application Priority Data
Jun. 1, 2017 (DE) .................... 10 2017 112 086.6

(51) Int. Cl.
*A61F 2/16*      (2006.01)
*B29D 11/02*    (2006.01)
*A61F 2/00*      (2006.01)

(52) U.S. Cl.
CPC .......... *A61F 2/1654* (2013.01); *B29D 11/023* (2013.01); *A61F 2002/0081* (2013.01);
(Continued)

(58) Field of Classification Search
CPC ........ A61F 2/1654; A61F 2/15; A61F 2/1637; A61F 2/1659; A61F 2002/0081;
(Continued)

(56) References Cited

U.S. PATENT DOCUMENTS 4,781,718 A   11/1988   Lindstrom
4,889,421 A   12/1989   Cohen
(Continued)

FOREIGN PATENT DOCUMENTS

CN    1053301      7/1991
CN    1287899      12/2006
(Continued)

OTHER PUBLICATIONS

PCT/EP2018/062924, International Preliminary Report on Patentability dated Dec. 12, 2019. 16 Pages.
(Continued)

*Primary Examiner* — Paul B Prebilic
(74) *Attorney, Agent, or Firm* — Alston & Bird LLP

(57) ABSTRACT

An artificial eye lens (1) having an optical part (2) which has a first optical side (4) and an opposite, second optical side (5). The optical part (2) has a diffractive grating structure that contributes to an optical imaging property of the optical part (2). The diffractive grating structure is an amplitude grating (6) formed in the optical part (2) as a laser structure. A method for producing an artificial eye lens (1) where the amplitude grating (6) is produced with a laser apparatus (17), and a pulsed laser beam (22) having a pulse length of between 100 fs and 20 ps, a wavelength of between 320 nm and 1100 nm, a pulse repetition rate of between 1 kHz and 10 MHz, a focus diameter of less than 5 μm, and a power density of greater than $10^6$ W/cm$^2$.

21 Claims, 2 Drawing Sheets

(52) U.S. Cl.
CPC ............... *A61F 2002/1683* (2013.01); *A61F 2002/1689* (2013.01); *A61F 2240/001* (2013.01)

(58) Field of Classification Search
CPC ........ A61F 2240/001; A61F 2250/0026; A61F 2250/005; A61F 2250/0053; A61F 2250/0091; B29D 11/023
See application file for complete search history.

(56) References Cited

U.S. PATENT DOCUMENTS

| | | | |
|---|---|---|---|
| 4,976,732 | A | 12/1990 | Vorosmarthy |
| 5,100,226 | A | 3/1992 | Freeman |
| 5,142,411 | A | 8/1992 | Fiala |
| 5,895,422 | A | 4/1999 | Hauber |
| 8,231,673 | B2 * | 7/2012 | Sacharoff ............ A61F 9/00834 623/6.22 |
| 2004/0032566 | A1 | 2/2004 | Nakada et al. |
| 2006/0235514 | A1 | 10/2006 | Silvestrini |
| 2006/0246112 | A1 | 11/2006 | Snyder et al. |
| 2009/0198326 | A1 | 8/2009 | Zhou et al. |
| 2009/0234448 | A1 | 9/2009 | Weeber et al. |
| 2009/0287306 | A1 | 11/2009 | Smith et al. |
| 2010/0082017 | A1 * | 4/2010 | Zickler ................ A61F 2/1624 606/4 |
| 2010/0094414 | A1 * | 4/2010 | Downer ............... B29D 11/023 623/6.27 |
| 2011/0292335 | A1 * | 12/2011 | Schwiegerling ...... A61F 2/1656 351/159.44 |
| 2013/0268071 | A1 | 10/2013 | Vilupuru et al. |
| 2013/0297017 | A1 * | 11/2013 | Dick ................... A61F 2/1624 623/6.27 |
| 2014/0135920 | A1 | 5/2014 | Sahler et al. |
| 2014/0259657 | A1 | 9/2014 | Riall et al. |
| 2015/0073549 | A1 | 3/2015 | Webb et al. |
| 2015/0342725 | A1 | 12/2015 | Cuevas et al. |
| 2015/0378065 | A1 | 12/2015 | Knox et al. |
| 2016/0135947 | A1 | 5/2016 | Webb et al. |
| 2016/0220352 | A1 | 8/2016 | Choi et al. |
| 2016/0331519 | A1 | 11/2016 | Kahook et al. |
| 2017/0042665 | A1 | 2/2017 | Currie et al. |
| 2017/0119521 | A1 | 5/2017 | Kahook et al. |
| 2017/0143477 | A1 | 5/2017 | Christie et al. |

FOREIGN PATENT DOCUMENTS

| | | | |
|---|---|---|---|
| CN | 1514423 | 6/2008 | |
| CN | 202472154 U | 10/2012 | |
| CN | 203220483 U | 10/2013 | |
| CN | 102655823 | 4/2016 | |
| DE | 3740533 A1 | 6/1989 | |
| EP | 0589809 | 3/1994 | |
| EP | 1250609 A2 | 10/2002 | |
| WO | 9427169 A1 | 11/1994 | |
| WO | WO9427169 | 11/1994 | |
| WO | WO9525288 | 9/1995 | |
| WO | WO03107076 A1 * | 12/2003 | ........... A61F 2/1613 |
| WO | 2012138426 A2 | 10/2012 | |

OTHER PUBLICATIONS

PCT/EP2018/062920, International Preliminary Report on Patentability dated Dec. 12, 2019. 16 Pages.
PCT/EP2018/062921, International Preliminary Report on Patentability dated Dec. 12, 2019. 18 Pages.
PCT/EP2018/062920, International Search Report dated Dec. 6, 2018.
PCT/EP2018/062921, International Search Report dated Dec. 6, 2018.
PCT/EP2018/062924, International Search Report dated Aug. 13, 2018. 14 pages.
Pin Yang et al: Femtosecond laser-pulse-induced birefringence in optically isotropic glass. Journal of Applied Physics 95, 5280 (2004); doi: 10.1063/1.1707231. 5 pages.
CN 201880035896.3, First Office Action dated May 7, 2021. 16 pages.
DE 10 2017 112 086.6, Examination Report dated Mar. 16, 2018. 9 pages + translation 3 pages = 12 pages total.
U.S. Office Action of U.S. Appl. No. 16/616,878 dated Jul. 20, 2021; 10 pages.
U.S. Office Action of U.S. Appl. No. 16/616,881 dated Jul. 19, 2021; 15 pages.
U.S. Office Action of U.S. Appl. No. 16/616,028 dated Jun. 11, 2021; 12 pages.
CN 201880035881.7, First Office Action dated Jun. 2, 2021. 20 pages.
CN 201880035713.8, First Office Action dated May 27, 2021. 17 pages.

* cited by examiner

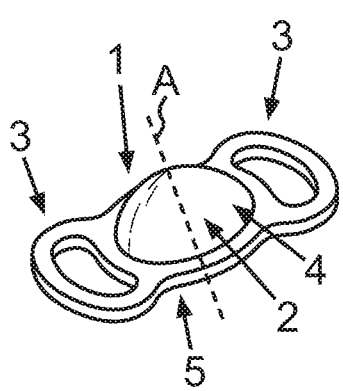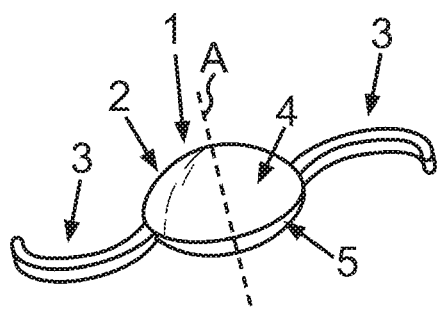
Fig.1a  Fig.1b
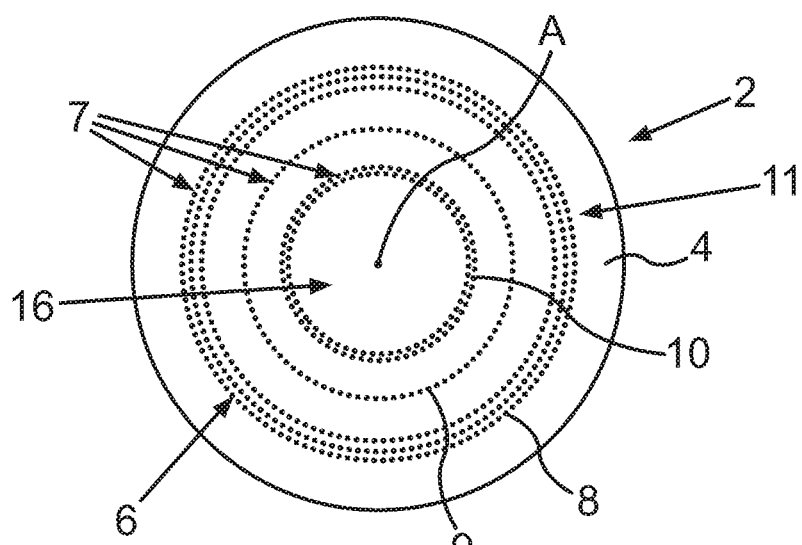
Fig.2
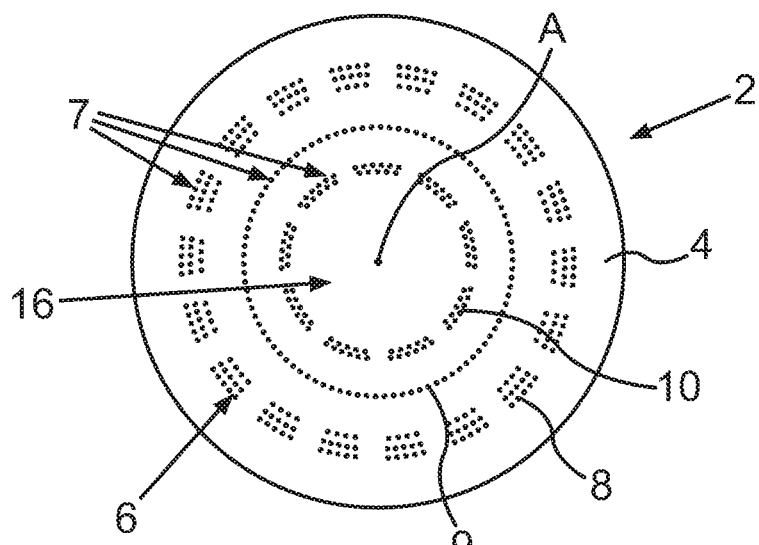
Fig.3

ARTIFICIAL EYE LENS WITH DIFFRACTIVE GRATING STRUCTURE AND METHOD FOR PRODUCING AN ARTIFICIAL EYE LENS

CROSS-REFERENCE TO RELATED APPLICATIONS

This application is a U.S. National Phase entry of International Application No. PCT/EP2018/062920, titled "Artificial eye lens with diffractive grating structure and method for producing an artificial eye lens," filed May 17, 2018, which claims priority to German Patent Application No. 10 2017 112 086.6, titled "Artificial eye lens with diffractive grating structure and method for producing an artificial eye lens", filed on Jun. 1, 2017, the contents of which are incorporated in this disclosure by reference in their entirety.

TECHNICAL FIELD

The invention relates to an artificial eye lens having an optical part which has, viewed in the direction of an optical principal axis of the artificial eye lens, a first optical side and an opposite, second optical side, wherein the optical part has a diffractive grating structure that contributes to the optical imaging property of the optical part. The invention furthermore also relates to a method for producing an artificial eye lens of this type using a laser.

PRIOR ART

A variety of multifocal, artificial eye lenses are known from the prior art. In particular known in this respect are intraocular lenses that replace the natural lens in the eye and are implanted relating thereto.

US 2010/0082017 A1 discloses an intraocular lens in which slits are made in a haptic part and also in an optical part to modify the mechanical characteristic and also the structure characteristic of the lens. Said elongate slits are formed in the interior of the intraocular lens, in particular using a laser.

Moreover, US 2004/0032566 A1 discloses a method for marking an intraocular lens using a laser. The laser is used to perform a micro-perforation of the optical part of the lens.

Moreover, US 2014/0135920 A1 discloses a production method for an intraocular lens in which a laser beam of an ultrashort pulse laser is used to change the hydrophilic behavior of the polymer material from which the artificial eye lens has been produced. With this change in the hydrophilic behavior of the polymer material, a reduction of the optical refractive index of this polymer material is produced.

A further known production method mentioned here is, for example, ultra-precision machining. In this case, a monocrystalline diamond tool is used since this tool also mechanically acts directly on the plastics material from which the eye lens is to be produced. This technology works with a geometrically determined, monocrystalline diamond tool corresponding to the conventional cutting methods such as turning or milling. However, highly stable machines and consistent environmental conditions are required for these production methods. Typically, here the manufacturing environment is air-conditioned and vibration-damped. Production is therefore highly complex.

Using ultra precision machining, it is possible, besides the aforementioned direct machining of the plastics optical units, to provide molding tools with which the eye lens can be molded in an injection-molding process, which is also less expensive.

The production of highly complex profiles on the surface of an optical part is here very limited, however, and the production of optically effective structures in the interior of the optical part is not possible. Structures produced with a laser have advantages over the former.

In known artificial eye lenses, in particular in intraocular lenses, undesirable orders of diffraction that limit the optical functionality thereof occur. These undesirable orders of diffraction also occur to a greater or lesser extent independently of the known production methods. Especially halos and glares can be mentioned here as disturbing impairments. The term halos denotes light effects which, as a result of refraction and reflection of light, generate for example halation around lamps, headlights and other light sources. They also occur in the form of rings of light. These are particularly undesirable effects especially in twilight or at night and may also lead to misperception. Halos occur at relatively sharp bright-dark transitions especially at twilight and at night, as a result of which, besides dazzling of an eye, generally even vision is relatively taxing for an eye lens wearer. Dazzling effects are referred to as glares. They occur in particular under direct incidence of bright light, for example in twilight or when it is dark, if a bright light source radiates light in the direction of the observer. Directly incident or reflected sunlight also produces such dazzling effects.

PRESENTATION OF THE INVENTION

It is the object of the invention to provide an artificial eye lens and a method for producing an artificial eye lens, in which or with which the occurrence of disturbing light effects such as halos and glares is at least reduced.

One aspect of the invention relates to an artificial eye lens having an optical part by way of which the optical imaging property of the eye lens is characterized. Said optical part has a first optical side and a second side located opposite the former viewed in the direction of the optical principal axis of said eye lens. The artificial eye lens furthermore has a haptic arrangement. The haptic arrangement is used to keep the artificial eye lens in its position in an eye. The artificial eye lens has, in addition to or as an alternative to the haptic arrangement, a surround that at least partially surrounds the optical part and differs from the haptic arrangement. This surround is then neither a constituent part of the optical part nor is it a constituent part in particular of arms of a haptic arrangement if such a haptic arrangement is present.

The artificial eye lens has a diffractive grating structure that contributes to the optical imaging property of the optical part. The diffractive grating structure is formed in the optical part of the artificial eye lens. Said diffractive grating structure is an amplitude grating which moreover is formed as a laser structure in the optical part of the artificial eye lens, which is in particular formed as one piece. An amplitude grating is an absorbing grating. An amplitude grating is configured such that it modulates the amplitude of the incident light wave. An amplitude grating is an optical grating that partially absorbs incident light.

An amplitude grating can be embodied in the form of a transmission grating or a reflection grating. By configuring such a specific optical grating as a laser structure, it is, firstly, producible with great precision, and, secondly, it can be produced locally with great definition at different locations of the optical part. Owing to the specific configuration of such an amplitude grating, undesirable orders of diffraction of the artificial eye lens can be suppressed. In particular, contrast enhancement of the optical system is also made possible thereby. In particular, it is also possible owing to such an embodiment of a diffractive grating structure in the form of an amplitude grating, formed as a laser structure, to at least noticeably reduce halos and glares in a particularly advantageous manner. Undesirable dazzling and reflection effects, as occur as a result of the specific, optically disturbing effects, can thereby be significantly reduced.

In one advantageous embodiment, the amplitude grating is configured as a micro-perforation in the optical part. This is a particularly advantageous embodiment when such a specific optical grating is produced as a laser structure. If an amplitude grating is produced by way of a micro-perforation, this makes possible a highly precise configuration of the individual structure regions of this amplitude grating. The optical effect of the amplitude grating is thereby achieved in a particularly advantageous manner. On the other hand, such a configuration achieves a very sharp definition of the contour regions of the amplitude grating, with the result that regions of the optical part that no longer belong to the amplitude grating especially at peripheral regions of the amplitude grating are not adversely impaired and the optical imaging properties thereof are not adversely falsified. It is also possible, especially owing to the configuration as a micro-perforation, to produce very finely metered differences in the structure regions of the amplitude grating, with the result that highly individual optical imaging properties of the amplitude grating in themselves can be produced here too.

Owing to a configuration of the amplitude grating as a micro-perforation, it is also possible in a particularly advantageous manner to create the configuration of the amplitude grating located inside in the optical part. In an embodiment which is advantageous in this respect, the amplitude grating is thus located entirely in the interior of the optical part and thus does not occur as a surface structure. Owing to this configuration, the amplitude grating by itself is also entirely surrounded by the material of the optical part and is formed only by perforation of the material of the optical part and the action of the laser radiation. This configuration of the amplitude grating, which is located inside and is thus embedded, makes the aforementioned advantages possible to a particular extent and moreover also creates the situation whereby the amplitude grating is protected against adverse mechanical influences. Therefore, especially when producing the artificial eye lens and then during further storage before implanting the artificial eye lens, no direct mechanical influences on this amplitude grating can occur and thus no damage to this amplitude grating can be caused either.

In a further advantageous embodiment, the amplitude grating has a first grating region configured with a first perforation density of perforation zones of the micro-perforation and/or with a first dimensioning of perforation zones of the micro-perforation. The amplitude grating in particular has a second grating region configured with a second perforation density of perforation zones of the micro-perforation that differs from the first perforation density of perforation zones and/or with a second dimensioning of perforation zones of the micro-perforation that differs from the first dimensioning of perforation zones of the micro-perforation. In this way, highly precise and thus optically highly functional amplitude grating regions can be created that can also be configured to be relatively small and/or form-specifically individual. In this way, the amplitude grating can also be configured with different attenuation degrees or gray levels and consequently with entirely individual absorption values for the incident light. The aforementioned undesirable optical refraction and reflection effects can thereby be reduced further.

In particular, it is also possible to configure a position and/or a number of opaque grating regions of the amplitude grating in dependence on said parameters, specifically the perforation density of the perforation zone of the micro-perforation and/or the dimensioning of perforation zones of the micro-perforation. The dimensioning of a perforation zone can be an inside dimension and/or a depth. Depending on the shape of such a perforation zone, it is thus possible to realize individual configurations of the amplitude grating.

In one advantageous embodiment, provision may be made for at least one perforation zone of the micro-perforation to be at least partially filled with a dye. With such an additional material, the amplitude grating can be improved further and be realized with different and more finely graduated attenuation degrees or gray levels. Moreover, the variability and flexibility of the grating structure are increased. Not least, it is possible to write with a particularly high precision of the grating structures in the micrometre range. The optical functionality of the amplitude grating can here be influenced entirely individually by specific absorbing dyes. Individual perforation zones can thus be at least partially filled with this dye and/or different dyes which absorb differently. The primary functionality of an amplitude grating, specifically individual absorption behavior in different regions, can here be designed individually in a highly variable and extremely flexible manner. This is made possible in particular also by the embodiment of the amplitude grating as a laser structure, because different perforation zone densities and different sizes of the perforation zones can here also be configured with great accuracy and thus precisely in terms of position and form. Filling, which may then be individual, with one or more dyes having individual absorption behaviors also allows particularly different and finely metered absorption behaviors of an amplitude grating to be obtained.

In one advantageous embodiment, the dye is polymerized in at least one perforation zone. The long-term stability of the dye is thus improved. Polymerization can be effected for example by UV (ultraviolet) light or by multiphoton polymerization with laser light.

In particular, a position and/or a number of opaque grating regions of the amplitude grating is established in dependence on the type of the dye and/or in dependence on the quantity of the dye and/or in dependence on the number of the perforation zones that are at least partially filled with dye and/or in dependence on the position of the perforation zones that are at least partially filled with dye. The high variability already mentioned above and the degree of individualization of an amplitude grating that is able to be produced are thus significantly increased. This is made possible in particular by the embodiment of the amplitude grating as a laser structure, because the advantages with respect to the principle production of such an amplitude grating, which have already been presented extensively above, and with respect to the positional accuracy and high optical functionality are only made possible with a laser.

In one advantageous embodiment, the amplitude grating has grating rings as grating regions that at least partially extend around an optical principal axis of the optical part. With such structuring of the amplitude grating, it is specifically possible to create ring zones having an absorbing effect, which then also have a preferably symmetric configuration, viewed geometrically, around the optical principal axis and have a uniform effect with respect to the optical properties in this azimuthal direction.

In particular, the amplitude grating is configured to be located entirely inside in the optical part. That means that it is entirely surrounded by the material of the optical part and is thus configured to not be located outside and thus exposed on the optical sides of the optical part. The advantages achieved thereby have already been mentioned above.

An individual aperture stop with which the depth of field of the eye is increased can be formed with the above-mentioned embodiments.

In one advantageous embodiment, an optical grating structure that is separate from the amplitude grating is formed on at least one side of the optical part. The optical imaging properties can be improved by two separate optical grating structures, and in particular disturbing optical effects can be suppressed even more effectively. In particular, it is then also possible to better suppress different optical disturbing effects.

In particular, the further separate optical grating structure is a phase grating. Phase gratings are optical diffraction gratings that influence the phase of the incoming light wave. In contrast to an amplitude grating, which is an absorbing optical grating, a phase grating is a wave-reshaping grating that reshapes the wavefront of the incident light source. A phase grating can also be embodied in the form of a transmission grating or a reflection grating. Especially in combination with an amplitude grating it is possible to improve the optical imaging properties and to more effectively reduce the aforementioned disturbing diffraction or reflection effects, in particular also relating to the aforementioned halos and glares, which can be at least noticeably reduced substantially by the amplitude grating, different disturbing diffraction effects and reflection effects.

In a further highly advantageous embodiment, provision is made for this phase grating to be achromatized for at least two wavelengths. In this way, the diffraction efficiency for specific orders of diffraction is maximized. To this end, as much intensity as possible is concentrated into specific desirable orders of diffraction, and, by contrast, minimized in the remaining orders of diffraction, for example including the zero order of diffraction. With an advantageous embodiment it is ensured that in specific grating regions of this phase grating a specific refractive index modification is produced to configure said achromatization for at least two wavelengths. This refractive index modification is produced with a laser, in particular an ultrashort pulse laser. Owing to an achromatization, the phase difference of the interfering waves are made dependent on the wavelength. This is done in the stated advantageous embodiment for at least two different wavelengths.

The above-mentioned phase grating can be a blazed grating, for example.

Provision may be made for at least one optical side of the optical part, as they were referred to above, to be configured to be spherical or aspheric. It is then possible for a toric configuration and thus a toric surface profile to be configured at least on one of said optical sides. Other optical surface profiles can also be configured on such an optical side of the optical part. For example, ring-shaped zones can be formed, which can be a constituent part of a further diffractive element. However, these ring-shaped zones are then formed on said optical side and are consequently optical structure elements that are located outside and are thus exposed.

The optical part of the artificial eye lens is then processed in particular using an ultrashort pulse laser of a laser apparatus in a manner such that the amplitude grating and possibly at least one further optical grating are produced. In particular, the parameters of the laser apparatus are set such that laser disruption in the transparent plastic of the optical part of the artificial eye lens occurs in the focal point of the laser beam just above the threshold value. If an increase in intensity of the laser beam is set, greater damage volumes are produced in this plastic. The laser disruptions that typically occur in the form of a bubble formation in the plastic can be produced in a single shot with sufficient energy, for example in the microjoule range, or with low energy density in the nanojoule range by way of a high repetition rate in the kilohertz to megahertz range.

In one advantageous embodiment, provision may also be made for the artificial eye lens to have a further optical grating structure that is configured as a holographic grating. Provision can be made in one advantageous embodiment for this grating structure to have a first holographic grating and a second holographic grating. In particular, a Moiré structure can be produced by way of these two holographic gratings. Preferably, a distance, measured in the direction of the optical principal axis, between the two holographic gratings is configured to be smaller than the distance, measured in the direction of the optical principal axis, between the first optical side and the second optical side. In particular, at least one holographic grating in the optical part of the artificial eye lens is configured to be located entirely inside between the optical sides of the optical part.

Provision may be made for at least one coating to be applied on the first optical side or on the second optical side of the optical part and for at least one holographic grating to be formed in said coating. The optical part can have at least one laminated region, and at least one holographic grating is formed in said laminated region.

In particular, said holographic grating is also formed as a laser structure in the optical part.

It is possible with such a specific configuration of a grating structure, in particular with at least two different separate holographic gratings that are in particular specifically superposed, to produce an individual refractive power of the eye lens. In order to be able to produce said optically active grating structure, preferably Moiré structure, within the coherence length of the light, at least two such diffractive structures in the form of the holographic gratings are produced as a laser structure using a laser, in particular within correspondingly adjacent layers of an optical part of the eye lens. It is possible here to produce in the plastic a positive and a negative change of the refractive index.

The artificial eye lens is in particular a multifocal, in particular at least trifocal, artificial eye lens. The artificial eye lens is in particular an intraocular lens. In particular, the optical part of the artificial eye lens is formed as one piece. The optical part preferably has a diameter of greater than 2 mm, in particular greater than or equal to 3 mm. The amplitude grating in the optical part is formed at a radial distance of greater than or equal to 1 mm from the optical principal axis.

The invention furthermore also relates to a method for producing a multifocal, artificial eye lens according to the aforementioned aspects, in which an optically effective structure is produced with a laser apparatus, and a pulsed laser beam having a pulse length of between 100 fs and 20 ps, a wavelength of between 320 nm and 1100 nm, a pulse repetition rate of between 1 kHz and 10 MHz, a focus diameter of less than 5 µm, in particular of less than 2 µm, and a power density of greater than $10^6$ W/cm$^2$ is produced and acts on the material of the artificial eye lens. The pulse length is preferably 300 fs and the wavelength is preferably 1060 nm or 532 nm or 355 nm. By way of a disruptive machining, it is possible for preferably a wavelength of 256 nm and preferably of 213 nm to be provided for in particular ablative machining.

Further features of the invention are evident from the claims, the figures and the description of the figures. The features and feature combinations mentioned in the description above and the features and feature combinations mentioned in the description of the figures below and/or only shown in the figures may be used not only in the respectively specified combination, but also in other combinations, without departing from the scope of the invention. Hence, embodiments of the invention which are not explicitly shown and explained in the figures but which emerge from the explained embodiments by way of separate feature combinations and which are producible should also be considered to be comprised and disclosed. Therefore, embodiments and feature combinations which do not have all the features of an originally phrased independent claim should also be considered to be disclosed. Furthermore, embodiments and feature combinations, in particular by virtue of the embodiments explained above, which go beyond or deviate from the feature combinations explained in the dependency references of the claims should be considered to be disclosed.

The concrete values indicated in the documents for parameters and indications concerning ratios of parameters or parameter values for the definition of exemplary embodiments of the eye lens should be considered to be concomitantly encompassed by the scope of the invention even in the context of deviations, for example on account of measurement errors, system faults, DIN tolerances, etc., which means that explanations relating to substantially corresponding values and indications should also be understood thereby.

BRIEF DESCRIPTION OF THE DRAWINGS

Exemplary embodiments of the invention are explained in greater detail below with reference to schematic drawings. In the figures:

FIG. 1a shows a perspective schematic and simplified illustration of a first exemplary embodiment of an artificial eye lens according to the invention;

FIG. 1b shows a perspective schematic and simplified illustration of a further exemplary embodiment of an artificial eye lens according to the invention;

FIG. 2 shows a plan view of an exemplary embodiment of an optical part of an artificial eye lens with a specific first amplitude grating;

FIG. 3 shows a plan view of an exemplary embodiment of an optical part of an artificial eye lens with a specific second amplitude grating;

PREFERRED EMBODIMENTS OF THE INVENTION

Figure 4:
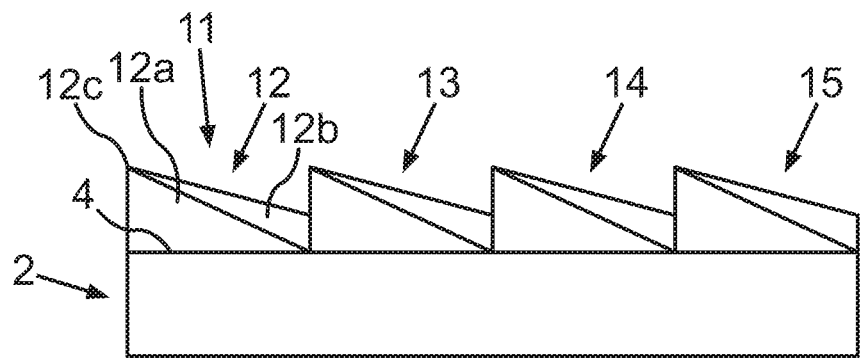
FIG. 4 shows a schematic sectional illustration of an exemplary embodiment of an artificial eye lens with a phase grating in the optical part.

In the figures, identical or functionally equivalent elements are provided with the same reference signs.

FIG. 1a shows a perspective illustration of a first exemplary embodiment of an artificial eye lens 1, which is in this case an intraocular lens. The artificial eye lens 1, referred to below as eye lens 1, comprises an optical part 2 and, adjacent thereto, a haptic arrangement 3. The eye lens 1 is multifocal, in particular trifocal. The eye lens 1 is foldable and may be introduced into an eye through a small incision. The optical part 2, which is essential for the optical imaging property of the eye lens 1, comprises an optical principal axis A. Furthermore, as viewed in the direction of said optical principal axis A, the optical part 2 has a first optical surface or optical side 4, which can be a front side, and opposite thereto has a second optical surface or optical side 5, which can be a rear side. In the implanted state of the eye lens 1 in the eye, the front side faces the cornea, whereas the rear side faces away from this cornea.

FIG. 1b shows a perspective illustration of a further exemplary embodiment of an artificial eye lens 1 formed as an intraocular lens. Said lens differs from the embodiment in FIG. 1a by way of the different haptic arrangement 3. The eye lens 1 is held in the eye by means of the haptic arrangement 3.

In the embodiments, the optical sides 4 and 5 are curved in a non-planar fashion, in particular convexly. On at least one optical side 4, 5, a diffractive profile is formed on this convex basic shape.

In principle, it is also possible for differently shaped and configured haptic arrangements 3 to be provided.

FIG. 2 shows a simplified illustration of the optical part 2 with a view of the optical side 4. The eye lens 1 could additionally or alternatively also be configured accordingly with a view of the optical side 5. In the exemplary embodiment, a diffractive grating or a diffractive grating structure, which is an amplitude grating 6, is preferably formed inside the optical part 2, which preferably has the shape of a disk. The amplitude grating 6 is formed as a laser structure. The amplitude grating 6 is in particular arranged completely within the optical part 2 and produced by way of a laser. The amplitude grating 6 is therefore surrounded entirely by the remaining material of the optical part 2 and is thus enclosed completely by said material.

The optical part 2 is formed in one piece and thus from a single part.

In particular, the amplitude grating 6 can also be configured as a micro-perforation 7 in the optical part 2.

The amplitude grating 6 has a first grating region 8 configured with a first perforation density of perforation zones of the micro-perforation 7 and/or with a first dimensioning of perforation zones of said micro-perforation 7. The amplitude grating 6 preferably has a second grating region 9, which is separate therefrom and configured with a second perforation density of perforation zones of the micro-perforation 7 that differs from the first perforation density of perforation zones of the micro-perforation 7 and/or with a second dimensioning of perforation zones of the micro-perforation 7 that differs from the first dimensioning of perforation zones of the micro-perforation 7. In particular, provision is made for the amplitude grating 6 to also have at least a third grating region 10, which is configured with a third perforation density of perforation zones that differs from the first and second perforation densities of perforation zones of the micro-perforation 7 and/or with a third perforation density of perforation zones and/or dimensioning of perforation zones of the micro-perforation 7 that differs from the first and second dimensioning of perforation zones of the micro-perforation 7.

Provision may be made for at least one grating region 8, 9, 10 to repeat in the radial direction with respect to the optical principal axis A, which is perpendicular to the figure plane. An alternating arrangement in this radial direction with respect to the optical principal axis A of at least two grating regions 8, 9, 10 can also be provided.

In the embodiment shown according to FIG. 2, the individual perforation zones of the micro-perforation 7 are formed as ring zones that are configured to extend in particular completely around the optical principal axis A. It is also possible for a configuration to be provided in which at least one grating region 8, 9, 10 is configured to extend only partially around the optical principal axis A.

As can be seen, the radial thickness of a grating region 8, 9, 10 is also configured such that it differs.

Provision is in particular made for at least one dye to be contained in at least one perforation zone, preferably in a plurality of perforation zones, of at least one grating region 8, 9, 10. The absorption behavior of the amplitude grating 6 can thus be set differently.

Provision may be made for the at least one absorbing dye in at least one perforation zone to be polymerized.

In one advantageous embodiment, provision is made for a further optical grating structure to be additionally formed as a grating structure that is separate from the amplitude grating 6 on the optical side 4 and/or on the optical side 5 and consequently located outside. Said further grating structure is configured as a separate optical grating and in particular configured as a phase grating 11. For the sake of clarity, this phase grating 11 is not explicitly structurally shown in FIG. 2, but merely indicated with a reference sign.

Reference is made to the highly simplified and schematic illustration in FIG. 4 for a possible embodiment of the phase grating 11. Here, a detail of the optical part 2 is shown and a highly simplified sectional illustration of the optical part 2 is shown, wherein the optical principal axis A is located in said sectional plane.

The phase grating 11 is shown here as a blazed grating as an example. In particular, the optical side 4 and the optical side 5 are each configured to be non-planar, in particular configured to be curved, wherein a spherical or aspheric curvature may be formed here. In the greatly enlarged cross-sectional view of FIG. 4, the optical side 4 is not curved but illustrated in simplified fashion in a planar state.

FIG. 4 shows an example in which the phase grating 11 is formed on the optical side 4. This phase grating 11 is also formed as a laser structure and produced with the laser apparatus which will be explained below. The phase grating 11 has a plurality of grating regions 12, 13, 14 and 15. The grating regions 12 to 15 should be understood to be merely an example, and to be schematic and not exclusive, in terms of number and also in terms of their individual form. The grating regions 12 to 15 are formed as graduated zones with respect to one another. Provision is preferably made for the phase grating 11 to be achromatized for at least two wavelengths.

Provision is in particular made for the grating region 12 to have a first partial region 12a and a second partial region 12b. The two partial regions 12a and 12b have different refractive indices. This is achieved by the action of a laser beam on the material of the optical part 2. In principle, the phase grating 11 is advantageously formed from the same material as the optical part 2. Under the action of a laser beam, in particular the partial region 12b that is located further outside is influenced in a manner such that the refractive index changes, wherein a change in the material configuration is produced here by said laser beam and results in a change of the refractive index. The partial region 12a, by contrast, has in particular the unchanged refractive index in accordance with the material of the optical part 2. As is evident in the embodiment in FIG. 4, which is likewise to be understood to be non-limiting, the outer partial region 12b that has been changed in terms of its refractive index by the action of the laser beam is in this cross-sectional illustration formed in the shape of a triangle. Viewed from a zone tip 12c, it widens in the direction of the adjacent second grating region 13 and then has its maximum expansion in particular at the preferably formed joining location at the adjacent grating region 13.

In particular, a corresponding configuration is also formed in at least one further grating region 13 to 15, as is likewise indicated in FIG. 4.

FIG. 3 shows a likewise simplified illustration of the optical part 2 of a further exemplary embodiment of the artificial eye lens 1. In contrast to the illustration as per FIG. 2, provision is made here for the configuration of the amplitude grating 6, which is additional to the birefringent structure 2a, not to be configured with surrounding rings as grating regions 8, 9, 10, but for it to be produced by a plurality of individual local regions that are configured to be spaced apart and preferably equidistant with respect to one another in the circumferential direction around the optical principal axis A. The individual local regions are here also formed by in each case a plurality of perforation zones that can likewise be at least partially filled in particular with one or more dyes. As can be seen here, the grating region 8 has a plurality of local regions that are formed in an individual configuration differently from local regions of the grating region 10 that is located for example further inside. In particular, provision may also be made for a grating region, in the present case the grating region 9, to be realized in accordance with the configuration in FIG. 2. A further alternative can likewise be configured such that for example the grating region 8 is configured accordingly in FIG. 2 and only the grating region 10 is configured according to the illustration in FIG. 3. Provision may likewise be made for the grating region 10 to be realized according to the configuration in FIG. 2 and only the grating region 8 to be realized according to the configuration in FIG. 3. Provision may likewise be made for the grating region 9 to be correspondingly configured to be interrupted in individual local regions, as is provided in the embodiments in FIG. 3 for the grating regions 8 and 10.

In addition to the amplitude grating 6 and in addition or as an alternative to the possibly present phase grating 11, a further optically effective grating structure 16 (FIG. 2 and FIG. 3) can also be formed on or in the optical part 2. This further separate optical grating structure 16 has at least one holographic grating. This further optical grating structure 16 is preferably formed as a laser structure and is produced in particular with the laser apparatus, as will be explained below with respect to FIG. 5.

This optical structure 16 preferably has two separate holographic gratings, a first holographic grating and a second holographic grating. Preferably, a distance, measured in the direction of the optical principal axis A, between the two holographic gratings is configured to be smaller than the distance, measured in the direction of the optical principal axis A, between the first optical side 4 and the second optical side 5. In one advantageous embodiment, the at least two holographic gratings are superposed and in particular superposed such that a Moiré structure is formed. In particular, this optical structure 16 is configured as a central circular zone around the optical principal axis A of the optical part 2.

Figure 5:
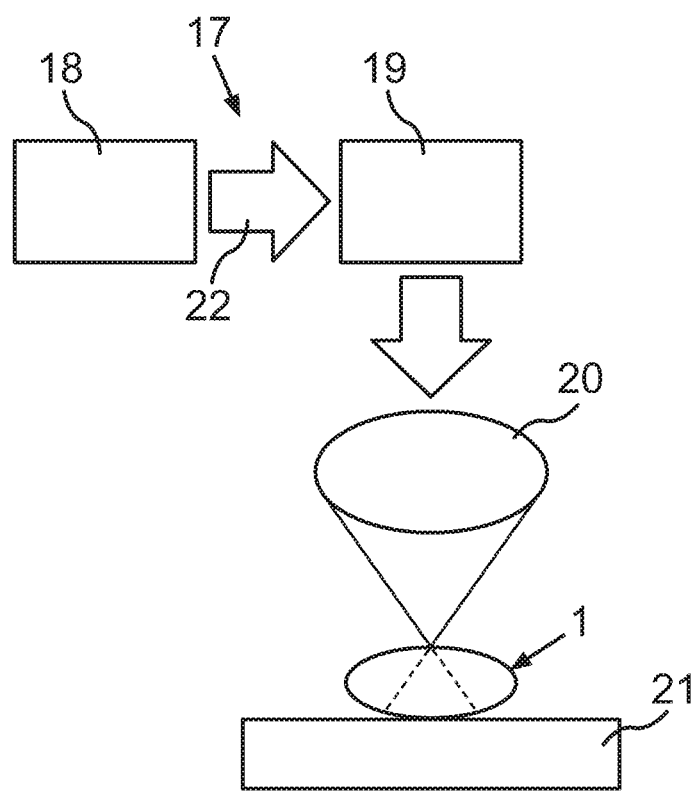
FIG. 5 shows a simplified illustration of a laser apparatus for producing an artificial eye lens.

FIG. 5 shows a schematic illustration of a laser apparatus 17, which is configured for producing a multifocal, artificial eye lens 1. In particular, this laser apparatus 17 can be used to produce the amplitude grating 6 and/or the phase grating 11 and/or the at least one further optical grating structure 16. The laser apparatus 17 has at least one laser 18, which is an ultrashort pulse laser. Said laser apparatus 17 has an in particular 3-dimensionally settable scanner 19, with which a pulsed laser beam of the laser 18 is settable. The laser apparatus 17 furthermore has a focusing optical unit 20 arranged downstream of the scanner 19 in the beam path. The laser apparatus 17 furthermore has a receptacle 21 on which the artificial eye lens 1 is placed so as to be able subsequently to allow the desired structuring to form with the laser beam 22 focused by way of the focusing optical unit 20. The pulsed laser beam 22 with its laser pulses is produced in particular with a pulse length of between 100 fs and 20 ps, in particular a wavelength of between 200 nm and 1100 nm, in particular a pulse repetition rate of between 1 kHz and 10 MHz, in particular a focus diameter of less than 5 µm, and in particular a power density of greater than $10^8$ W/cm$^2$. In particular, multiphoton absorption is made possible here. The focusing optical unit 20 can have a numerical aperture of greater than 0.1, preferably greater than 0.3, and in particular greater than 0.5. The production of focus diameters of less than 5 µm, in particular of less than 2 µm, is also possible with the laser apparatus 17. In this case, a power density of the focused laser beam of greater than $10^{10}$ W/cm$^2$ is appropriate for achieving an optical disruption (photodisruption) of the polymer material of the artificial eye lens when for example no linear absorption of the polymer material supports this effect. In order to achieve only a non-linear interaction in the polymer material of the artificial eye lens 1, a power density of less than $10^{10}$ W/cm$^2$ is also provided, which does not result in photodisruption, but can change optical and/or mechanical or associated hygroscopic material properties. In order to ensure a high machining efficiency of the artificial eye lens, a repetition rate of the ultrashort laser pulses of the laser beam 22 in the range of 1 kHz to 10 MHz is advantageous. Pulse energies in the sub-0 range are used here. In particular, at a repetition rate of greater than 1 MHz, a pulse energy of less than 1 µJ is also provided owing to cumulative interaction effects.

The invention claimed is:

1. An artificial eye lens having an optical part which has, viewed in the direction of an optical principal axis of the artificial eye lens, a first optical side and an opposite, second optical side, wherein the optical part has a diffractive grating structure that contributes to an optical imaging property of the optical part, wherein the diffractive grating structure is an amplitude grating formed at least partially as a bubble formation in the optical part between the first optical side and the second optical side as a laser-generated structure.

2. The artificial eye lens of claim 1, where the amplitude grating is formed at least partially as a micro-perforation in the optical part as a laser-generated structure.

3. The artificial eye lens of claim 2, where the amplitude grating has a first grating region configured with a first perforation density of perforation zones of the micro-perforation and a second grating region configured with a second perforation density of perforation zones of the micro-perforation that differs from the first perforation density of perforation zones.

4. The artificial eye lens of claim 3, further comprising a first dimensioning of perforation zones of the micro-perforation.

5. The artificial eye lens of claim 4, further comprising a second dimensioning of perforation zones of the micro-perforation that differs from the first dimensioning of perforation zones in the micro-perforation.

6. The artificial eye lens of claim 2, wherein the amplitude grating has a first grating region configured with a first dimensioning of perforation zones of the micro-perforation and a second grating region configured with a second dimensioning of perforation zones of the micro-perforation that differs from the first dimensioning of perforation zones of the micro-perforation.

7. The artificial eye lens of claim 2, wherein at least one perforation zone of the micro-perforation is at least partially filled with a dye.

8. The artificial eye lens of claim 7, wherein the dye is polymerized.

9. The artificial eye lens as claimed in claim 7, wherein a position of opaque grating regions of the amplitude grating is established in dependence on the type of the dye.

10. The artificial eye lens of claim 7, where a number of opaque grating regions of the amplitude grating is established in dependence on the type of the dye.

11. The artificial eye lens of claim 10, where the number of opaque grating regions of the amplitude grating is established in dependence on the quantity of the dye.

12. The artificial eye lens of claim 10, where the number of opaque grating regions of the amplitude grating is established in dependence on the number of the perforation zones that are at least partially filled with dye.

13. The artificial eye lens of claim 10, where the number of opaque grating regions of the amplitude grating is established in dependence on the position of the perforation zones that are at least partially filled with dye.

14. The artificial eye lens of claim 1, wherein the amplitude grating has grating rings that at least partially extend around an optical principal axis of the optical part as grating regions.

15. The artificial eye lens of claim 1, wherein the amplitude grating is configured to be located inside in the optical part.

16. The artificial eye lens of claim 1, wherein at least one optical grating structure that is separate from the amplitude grating is formed on at least one optical side.

17. The artificial eye lens of claim 16, wherein the separate optical grating structure is a phase grating.

18. The artificial eye lens of claim 17, wherein the phase grating is achromatized for at least two wavelengths.

19. A method for producing an artificial eye lens, the method comprising:
    causing an amplitude grating to be produced in an optical part of the artificial eye lens, wherein the optical part has, viewed in the direction of an optical principal axis of the artificial eye lens, a first optical side and an opposite, second optical side, with a laser apparatus that acts on the optical part, wherein the amplitude grating is formed, by the laser apparatus, at least partially as a bubble formation in the optical part between the first optical side and the second optical side.

20. The method of claim 19, wherein causing the amplitude grating to be produced in the optical part of the artificial eye lens comprises causing the laser apparatus to generate a pulsed laser beam having a pulse length between 100 fs and 20 ps, a wavelength of between 320 nm and 1100 nm, a pulse repetition rate of between 1 kHz and 10 MHz, a focus diameter of less than 5 µm, and a power density of greater than $10^6$ W/cm$^2$.

21. An artificial eye lens produced by causing an amplitude grating to be produced in an optical part of the artificial eye lens, wherein the optical part has, viewed in the direction of an optical principal axis of the artificial eye lens, a first optical side and an opposite, second optical side, with a laser apparatus by causing the laser apparatus to generate a pulsed laser beam that acts on the optical part to form the amplitude grating, wherein the amplitude grating is formed, by the laser apparatus, at least partially as a bubble formation in the optical part between the first optical side and the second optical side.

* * * * *